(12) United States Patent
Kratel et al.

(10) Patent No.: US 9,233,986 B2
(45) Date of Patent: Jan. 12, 2016

(54) METHOD FOR PRODUCING HYDROPHOBIC, HEAT-INSULATING MOULDINGS

(75) Inventors: Guenter Kratel, Durach (DE); Gerd Borchert, Durach (DE); Frank Menzel, Hanau (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/233,085

(22) PCT Filed: Jul. 27, 2011

(86) PCT No.: PCT/EP2011/062932
§ 371 (c)(1),
(2), (4) Date: Jan. 15, 2014

(87) PCT Pub. No.: WO2013/013714
PCT Pub. Date: Jan. 31, 2013

(65) Prior Publication Data
US 2014/0150242 A1  Jun. 5, 2014

(51) Int. Cl.
| | | |
|---|---|---|
| C07F 7/02 | (2006.01) | |
| C04B 30/02 | (2006.01) | |
| C04B 41/00 | (2006.01) | |
| C04B 41/49 | (2006.01) | |
| C04B 41/64 | (2006.01) | |
| C09C 1/30 | (2006.01) | |
| C04B 111/28 | (2006.01) | |

(52) U.S. Cl.
CPC ............... *C07F 7/025* (2013.01); *C04B 30/02* (2013.01); *C04B 41/009* (2013.01); *C04B 41/4933* (2013.01); *C04B 41/64* (2013.01); *C09C 1/3081* (2013.01); *C04B 2111/28* (2013.01); *Y02W 30/94* (2015.05); *Y02W 30/97* (2015.05); *Y10T 29/4998* (2015.01)

(58) Field of Classification Search
None
See application file for complete search history.

(56) References Cited

U.S. PATENT DOCUMENTS

| 5,705,239 A | * | 1/1998 | Andersen et al. | ............ 428/34.5 |
| 6,080,475 A | | 6/2000 | Frank et al. | |
| 2012/0286189 A1 | * | 11/2012 | Barthel et al. | ............... 252/62 |

FOREIGN PATENT DOCUMENTS

| DE | 10 2007 042 000 | 3/2009 |
| GB | 2 376 942 | 12/2002 |
| JP | 3-174377 | 7/1991 |
| JP | 6-157021 | 6/1994 |
| JP | 6-271371 | 9/1994 |
| JP | 6271371 | 9/1994 |
| JP | 2003-12380 A | 1/2003 |
| JP | 2004-227851 | 8/2004 |
| RU | 2 161 143 C2 | 12/2000 |
| WO | WO 01/47834 A1 | 7/2001 |
| WO | WO/2011/069923 | *  6/2011 |

OTHER PUBLICATIONS

International Search Report Issued Apr. 17, 2012 in PCT/EP11/062932 Filed Jul. 27, 2011.
L.A. Belyakova, et al., "Surfaces properties of silica gels modified with hydrophobic groups" Colloids and Surfaces A: Physicochemical and Engineering Aspects 154, 1999, pp. 285-294.

* cited by examiner

*Primary Examiner* — Joseph Miller, Jr.
(74) *Attorney, Agent, or Firm* — Oblon, McClelland, Maier & Neustadt, L.L.P.

(57) ABSTRACT

Process for hydrophobizing a microporous thermal insulation molding comprising hydrophilic silica, in which the molding is treated with at least one organosilane and in which one or more organosilanes which are gaseous under the reaction conditions are introduced into a chamber containing the microporous thermal insulation molding comprising hydrophilic silica until the pressure difference $\Delta p$ is $\geq 20$ mbar.

17 Claims, No Drawings

METHOD FOR PRODUCING HYDROPHOBIC, HEAT-INSULATING MOULDINGS

The invention relates to a process for producing hydrophobic, thermally insulating moldings under defined pressure conditions.

DE-A-3037409 discloses making thermal insulation materials composed of foamed perlites water-repellent by means of stearates, siliconates, waxes and fats. This is attributable to coating of the surface with these materials. Although the thermal insulation materials which have been treated this way repel liquid water, they absorb water vapor in the form of atmospheric moisture. This leads to a deterioration in the insulation properties.

DE-A-4221716 discloses reacting pyrogenic silicas with organosilanes and thereby making them water-repellent. However, such hydrophobic silica cannot be compressed sufficiently and is therefore not pressable. Pressing of a mixture provided with hydrophobic silica also does not lead to acceptable results.

EP-A-1988228 describes a process for pressing to form hydrophobic, microporous thermal insulation moldings by addition of organosilanes during a mixing process. A disadvantage of this process can be considered to be that pressing to form stable plates is possible only with very great difficulty, in particular when gaseous products are formed in the hydrophobization.

It was therefore a technical object of the invention to provide a process which minimizes the disadvantages occurring in the hydrophobization of thermal insulation materials and is also simple and economical to carry out.

The invention provides a process for hydrophobizing a microporous thermal insulation molding comprising hydrophilic silica, in which the molding is treated with at least one organosilane, wherein one or more organosilanes which are gaseous under the reaction conditions are introduced into a chamber containing the microporous thermal insulation molding comprising hydrophilic silica until the pressure difference $\Delta p$ is $\geq 20$ mbar.

$\Delta p = p2 - p1$, where $p1$=pressure in the chamber before introduction of the organosilane, $p2$=pressure in the chamber at which the introduction of the organosilane is stopped. The process of the invention is carried out so that preferably 50 mbar$\leq \Delta p \leq$5 bar, particularly preferably 100 mbar$\leq \Delta p \leq$500 mbar, very particularly preferably 200 mbar$\leq \Delta p \leq$400 mbar.

For the purposes of the present invention, a hydrophilic silica is a silica which on its surface bears no organic groups such as alkyl groups which could give it a hydrophobic, water-repellent character. Rather, the groups present on the surface should consist largely or entirely of Si—OH and Si—O—Si groups. Mention may be made by way of example of the preparation of pyrogenic silicas by flame hydrolysis, in which a gaseous silicon compound is burnt in a hydrogen/oxygen flame. This pyrogenic silica is hydrophilic.

The chamber merely has to meet the requirement that it can maintain the pressures required in the process of the invention.

In a particular embodiment of the invention, the process is carried out so that the pressure in the chamber before introduction of the organosilane is less than atmospheric pressure. In particular, it is advantageous when 0.1 mbar$\leq p1 \leq$atmospheric pressure. Particular preference is given to a variant in which 1$\leq p1 \leq$500 mbar. In this preferred embodiment, the organosilane is thus introduced into an evacuated chamber. In this subatmospheric pressure process, the organosilane is itself "sucked" into the finest pores of the hydrophilic molding and optimally distributed therein.

In a further preferred embodiment of the invention, the process is carried out with the pressure in the chamber before introduction of the organosilane being atmospheric pressure or above. In this case, it is advantageous when atmospheric pressure$\leq p1 \leq$10 bar. In this superatmospheric pressure process, the organosilane is "pushed" into the pores of the hydrophilic thermal insulation molding and thereby optimally distributed.

As microporous, hydrophilic silica in the process of the invention, preference is given to using a pyrogenic silica and/or a silicon dioxide aerogel.

Silicon dioxide aerogels are produced by specific drying processes from aqueous silicon dioxide gels. They likewise have a very high porosity and are therefore highly effective insulation materials.

Pyrogenic silicas are produced by flame hydrolysis of volatile silicon compounds such as organic and inorganic chlorosilanes. In this process, a hydrolyzable silicon halide in vaporized or gaseous form is reacted with a flame formed by combustion of hydrogen and an oxygen-containing gas. The combustion flame provides water for the hydrolysis of the silicon halide and sufficient heat for the hydrolysis reaction. A silica prepared in this way is referred to as pyrogenic silica. In this process, primary particles which are virtually free of internal pores are firstly formed. These primary particles fuse during the process via "sintering necks" to form aggregates. Owing to this structure, pyrogenic silica is an ideal thermal insulation material since the aggregate structure brings about sufficient mechanical stability, minimizes heat transfer by solid-state conductivity via the "sintering necks" and produces a sufficiently high porosity.

The organosilanes used react with the silanol groups of the hydrophilic silica and in this way make the thermal insulation molding water-repellent.

For the process of the invention, one or more organosilanes can preferably be selected from the group consisting of $R_n$—Si—$X_{4-n}$, $R_3$Si—Y—$SiR_3$, $R_nSi_nO_n$, $(CH_3)_3$—Si—(O—Si$(CH_3)_2)_n$—OH, HO—Si$(CH_3)_2$—(O—Si$(CH_3)_2)_n$—OH, where n=1-8; R=—H, —$CH_3$, —$C_2H_5$; X=—Cl, —Br; —$OCH_3$, —$OC_2H_5$, —$OC_3H_8$, Y=NH, O.

Explicit mention may be made of $(CH_3)_3$SiCl, $(CH_3)_2$SiCl$_2$, $CH_3$SiCl$_3$, $(CH_3)_3$SiOC$_2$H$_5$, $(CH_3)_2$Si(OC$_2$H$_5)_2$, $CH_3$Si(OC$_2$H$_5)_3$, $(CH_3)_3$SiNHSi$(CH_3)_3$, $(CH_3)_3$SiOSi$(CH_3)_3$, $(CH_3)_8$Si$_4$O$_4$ [octamethyltetracyclosiloxane], $(CH_3)_6$Si$_3$O$_3$ [hexamethyltricyclosiloxane] and $(CH_3)_3$Si(OSi$(CH_3)_2)_4$OH [low molecular weight polysiloxanol]. Preference is given to using $(CH_3)_3$SiCl, $(CH_3)_2$SiCl$_2$, $CH_3$SiCl$_3$, $(CH_3)_3$SiNHSi$(CH_3)_3$ and $(CH_3)_8$Si$_4$O$_4$.

The process of the invention is, inter alia, characterized in that the organosilane is gaseous under the reaction conditions prevailing in the chamber. The organosilane itself can be introduced in liquid or vapor form into the chamber. When introduced in liquid form, for instance by spraying in, it should go over into the vapor state in the chamber. Preference is given to introducing an organosilane in vapor form.

The process can also be carried out by introducing polar substances into the chamber during or after the introduction of the organosilane. These substances can preferably be water, alcohols and hydrogen halides.

The microporous thermal insulation molding comprising hydrophilic silica which is used in the process of the invention can additionally contain opacifiers, fibers and/or finely divided inorganic additives.

Possible opacifiers are titanium oxides, zirconium oxides, ilmenite, iron titanate, iron oxides, zirconium silicate, silicon carbide, manganese oxide and carbon black. These opacifiers preferably have a maximum in the range from 1.5 to 10 µm in the infrared spectrum. The particle size of these particles is preferably 0.5-15 µm. They are present in the total mixture in a proportion of preferably from 5 to 20% by weight.

For reinforcement, i.e. for mechanical strengthening, fibers are used. These fibers can be inorganic or organic in nature and make up up to 12% by weight of the mixture. Examples of inorganic fibers which can be used are glass wool, rock wool, basalt fibers, slag wool and ceramic fibers consisting of melts of aluminum and/or silicon dioxide, and also further inorganic metal oxides. Pure silicon dioxide fibers are, for example, silica fibers. Examples of organic fibers which can be used are cellulose fibers, textile fibers or polymer fibers. The diameter of the fibers is preferably 1-12 µm, particularly preferably 6-9 µm, an the length is preferably 1-25 mm, particularly preferably 3-10 mm.

Furthermore, inorganic filler materials can be added in the process of the invention. Use can be made of various, synthetically produced modifications of silicon dioxide, e.g. precipitated silicas, electric arc silicas, $SiO_2$-containing fly dusts which are formed by oxidation of volatile silicon monoxide and are formed in the electrochemical preparation of silicon or ferrosilicon. Silicas produced by leaching of silicates such as calcium silicate, magnesium silicate and mixed silicates such as olivine with acids are likewise suitable. It is also possible to use naturally occurring $SiO_2$-containing compounds such as diatomaceous earths and kieselguhrs. Thermally expanded minerals such as perlites and vermiculites, finely divided metal oxides such as aluminum oxide, titanium dioxide, iron oxide can likewise be added.

In a particular embodiment of the invention, the microporous thermal insulation molding containing hydrophilic silica contains 45-95% by weight, preferably 55-90% by weight, of pyrogenic silicon dioxide and/or silicon dioxide aerogel, 5-20% by weight, preferably 7-15% by weight, of opacifiers, 5-35% by weight, preferably 10-30% by weight, of finely divided inorganic additives and 0-12% by weight, preferably 1-5% by weight, of fibers.

To accelerate the process, the thermal insulation molding to be treated can additionally be perforated. The perforation channels enable the organosilanes used in each case to be brought more quickly and in a targeted manner into the thermal insulation molding. Any excesses or reaction products to be removed can likewise be removed again in an accelerated manner through the perforation channels. The perforation can be carried out by needling the thermal insulation molding to be treated, preferably by means of needle grippers during actual pressing of the thermal insulation molding. Primarily in the case of thermal insulation boards, perforation can be carried out on one side but preferably on both sides. The hole depth depends on the thickness of the hydrophilic thermal insulation molding and can be in the range from 5 mm to all the way through, preferably about ⅔ of the thickness of the hydrophilic thermal insulation molding. To avoid heat bridges, two-sided perforation with an offset pattern of holes should preferably be carried out with the hydrophilic thermal insulation molding not being punctured all the way through. The diameter of a perforation channel should be in the range from 0.1 mm to 3.0 mm, preferably from 0.5 mm to 1.0 mm. The spacing of the perforation channels can be in the range from 5 mm to 200 mm, and in the case of one-sided perforation the spacing of the channels should preferably be as great as the needle depth and in the case of two-sided perforation should preferably be twice the needle depth.

It can be advantageous for the temperature in the chamber to be from 20° C. to 300° C. The treatment time can be controlled by means of this. Depending on the type of organosilane used, it can be particularly advantageous to select a temperature in the range from 50 to 200° C.

It can likewise be advantageous to leave the microporous thermal insulation molding containing hydrophilic silica in the chamber for from 1 minute to 1 hour, particularly preferably from 2 to 20 minutes, from the point in time at which the organosilane is added.

After the treatment is complete, any excess organosilanes and reaction products can be removed from the now hydrophobic molding by heating. To effect mechanical stabilization and to improve handling, including dust-free handling, the hydrophobic molding can be enclosed in nonwovens and films, preferably shrink films.

The invention further provides for the use of the hydrophobized thermal insulation molding produced by the process of the invention for producing insulation in hollow building blocks, core insulation in multilayer building blocks, core insulation for composite thermal insulation systems for interior and exterior insulation of buildings, insulation in cavity wall masonry, insulation in furnace construction and vacuum insulation panels.

Fields of use for these hydrophobic thermal insulation moldings produced by the process of the invention are, inter alia, all applications in which the insulation materials are exposed to moisture or wetness.

EXAMPLES

Example 1

A microporous thermal insulation panel having a size of 250×250×20 mm and a weight of 184.4 g, corresponding to an overall density of 147.5 kg/m³, and a composition of 87.0% by weight of pyrogenic silica having a BET surface area of 300 m²/g, 9.0% by weight of flame black and 4.0% by weight of short chopped viscose fibers (ø 9 µm; L 6 mm) is present in a desiccator heated to about 100° C. The pressure in the desiccator is reduced to 15 mbar by means of a water pump. Hexamethyldisilazane in vapor form is subsequently introduced into the desiccator until the pressure increases to 300 mbar.

Example 2

A microporous thermal insulation panel having a size of 250×250×20 mm and a weight of 189.3 g, corresponding to an overall density of 151.4 kg/m³, and a composition of 87.0% by weight of pyrogenic silica having a BET surface area of 300 m²/g, 9.0% by weight of flame black and 4.0% by weight of short chopped viscose fibers (ø9 µm; L 6 mm) is present in a desiccator heated to about 100° C. The pressure in the desiccator is reduced to 15 mbar by means of a water pump. Dimethyldichlorosilane in vapor form is subsequently introduced into the desiccator until the pressure increases to 300 mbar.

The plates obtained as per examples 1 and 2 are completely water-repellent, have good mechanical stability and an unchanged low thermal conductivity.

The invention claimed is:
1. A process for hydrophobizing a molding, the method comprising:
perforating a microporous thermal insulation molding comprising hydrophilic silica, to obtain a perforated, microporous molding; and treating the perforated, microporous molding with at least one organosilane in a chamber, thereby obtaining a hydrophobized molding, wherein:

the at least one organosilane is gaseous under said treating and is introduced into the chamber until a pressure difference $\Delta p$ is $\geq 20$ mbar, wherein $\Delta p = p2-p1$, where p1=pressure in the chamber before introduction of the organosilane, p2=pressure in the chamber at which the introduction of the organosilane is stopped.

2. The process of claim 1, wherein pressure p1 is less than atmospheric pressure.

3. The process of claim 1, wherein pressure p1 is atmospheric pressure or above.

4. The process of claim 1, wherein the molding comprises at least one of a pyrogenic silica and a silicon dioxide aerogel as the hydrophilic silica.

5. The process of claim 1, wherein the at least one organosilane is selected from the group consisting of $R_n$—Si—$X_{4-n}$, $R_3$Si—Y—Si$R_3$, $R_n$Si$_n$O$_n$, $(CH_3)_3$—Si—(O—Si$(CH_3)_2)_n$—OH, and HO—Si$(CH_3)_2$—(O—Si$(CH_3)_2)_n$—OH, where n is a number of from 1 to 8;

R is —H, —CH$_3$, or —C$_2$H$_5$;

X is —Cl, —Br; —OCH$_3$, —OC$_2$H$_5$, or —OC$_3$H$_8$; and

Y is NH, or O.

6. The process of claim 1, wherein the at least one organosilane is introduced in liquid or vapor form into the chamber.

7. The process of claim 1, wherein at least one of water, an alcohol, and a hydrogen halide is introduced simultaneously with or subsequently to the at least one organosilane.

8. The process of claim 1, wherein the molding further comprises at least one of an opacifier, a fiber, and a finely divided inorganic additive.

9. The process of claim 8, wherein the molding comprises:

45-95% by weight of at least one of pyrogenic silicon dioxide and silicon dioxide aerogel, 5-20% by weight of the opacifier, 5-35% by weight of the finely divided inorganic additive, and 0-12% by weight of the fiber.

10. The process of claim 1, wherein said treating occurs at a temperature of from 20 to 300° C.

11. The process of claim 1, wherein the molding is left in the chamber for from 1 minute to 1 hour before introducing the at least one organosilane.

12. The process of claim 1, wherein the perforation is carried out by needling.

13. the process of claim 12, wherein the needling is carried out with needle grippers during actual pressing of the thermal insulation molding.

14. The process of claim 1, wherein the hole depth of the perforations is about ⅔ of the thickness of the thermal insulation molding comprising hydrophilic silica.

15. The process of claim 1, wherein the perforations are in the form of a channel having a diameter in the range of 0.1 mm to 3.0 mm.

16. The process of claim 1, wherein the pressure difference $\Delta p$ is greater than or equal to 100 mbar and less than or equal to 500 mbar.

17. The process of claim 1, wherein the pressure difference $\Delta p$ is greater than or equal to 200 mbar and less than or equal to 400 mbar.

* * * * *